United States Patent [19]

Cass et al.

[11] Patent Number: 4,911,988

[45] Date of Patent: Mar. 27, 1990

[54] PRESERVATIVE ELEMENTS CONTAINING ORGANIC BORON COMPOUNDS AND THEIR USE

[75] Inventors: Raymond C. Cass, New Malden, England; William K. H. Lakin, Manchester, England

[73] Assignee: Manchem Limited, London, England

[21] Appl. No.: 254,339

[22] Filed: Oct. 6, 1988

[30] Foreign Application Priority Data

Oct. 13, 1987 [GB] United Kingdom ................ 8724024

[51] Int. Cl.$^4$ ...................... B32B 21/04; C09K 15/32
[52] U.S. Cl. ................................. 428/537.1; 428/907; 428/704; 428/543; 428/541; 428/384; 428/366; 428/212; 424/405; 424/409; 424/408; 514/64; 106/18.3; 34/9.5; 252/400.41; 47/57.5; 568/1
[58] Field of Search ............... 428/366, 212, 541, 704, 428/384, 537.1, 543, 907; 34/9.5; 427/297, 308; 424/405, 409, 408; 47/57.5; 523/122; 252/400.41; 514/64; 106/18.3; 423/277; 568/1

[56] References Cited

U.S. PATENT DOCUMENTS

| | | | |
|---|---|---|---|
| 2,062,081 | 1/1936 | Zwingauer | 427/291 |
| 3,342,629 | 9/1967 | Martin | 34/9.5 |
| 3,519,713 | 7/1970 | Ludvik | 514/64 |
| 4,022,713 | 5/1977 | Waldstein | 252/389 |
| 4,269,875 | 5/1981 | Bechgaard et al. | 427/291 |
| 4,354,316 | 10/1982 | Schroeder | 428/541 |
| 4,661,157 | 4/1987 | Beauford et al. | 106/18.13 |
| 4,778,833 | 10/1988 | Van der Drift | 525/192 |

FOREIGN PATENT DOCUMENTS 2114003 8/1983 United Kingdom .

Primary Examiner—Ellis P. Robinson
Attorney, Agent, or Firm—James R. Thornton

[57] ABSTRACT

A preservative element, for timber or masonry in the form of a shaped element containing an organic boron compound, especially a boro-organic ester. Preferably the element also contains inorganic boron salts or acids, with or without the addition of other inorganic compounds having fungicidal and/or insecticidal properties.

20 Claims, No Drawings

PRESERVATIVE ELEMENTS CONTAINING ORGANIC BORON COMPOUNDS AND THEIR USE

SUMMARY OF INVENTION

This invention relates to new preservative elements containing organic boron compounds and their use to protect structural materials, particularly timber and masonry susceptible to infestation by fungi or insects.

BACKGROUND OF THE INVENTION

Inorganic boron compounds are well established as preservatives for timber and other materials against attack from fungi or insects. Recent developments have included the use of shaped rods, pellets or tablets of inorganic boron compounds for insertion into pre-formed cavities in timber. U.S. Pat. No. 4,269,875 describes shaped timber preservative elements comprising fused monolithic bodies of wood preservative containing boron compounds, particularly boric oxide. These elements are most suitable in the treatment of timber such as new joinery, prior to fungal attack as a protective rather than remedial treatment, as they are only slowly soluble and have extensive lives in situ. A disadvantage of these elements is that they are expensive as they are difficult to manufacture except by casting.

U.K. Patent 2,114,003 proposes preservative tablets of inorganic boron compounds which are shaped by compression to fit in pre-formed cavities in timber or other materials. These tablets dissolve more rapidly than the fused products of U.S. Pat. No. 4,269,875 in the moisture contained in the timber but suffer from the disadvantage of being mechanically weak except when prepared in the presence of a suitable adhesive binder such as starch.

Both the tablets and fused elements rely solely upon the moisture present in the location in which they are inserted within the timber to dissolve the preservative and transport it through the grain to the areas to be protected. Under some conditions this may lead to too little preservative being transported in time to prevent the onset of decay. This difficulty has been recognized and the use of highly concentrated solutions of inorganic borates and boric acid in glycols has been proposed to be used in conjunction with fused borate elements or borate tablets to overcome the problem. According to U.S. Pat. No. 4,610,881, the glycol assists the borate in penetrating the outer parts of the wood more rapidly.

Other shaped bodies of inorganic borates capable of binding water by hydration, and their use as preservatives, are described in U.S. Pat. No. 4,661,157.

DESCRIPTION OF THE INVENTION

According to the present invention a shaped preservative element is provided containing solid organic boron compounds which are hydrolysed in the presence of moisture.

The compounds having melting points preferably in the range of about 50°–200° C. These may be easily formed into shaped elements by fusion and casting or extrusion more easily and more economically than when the preservative element is composed of inorganic boron materials alone. This is particularly evident in the case of extrusion as they can be extruded at low temperatures by conventional means as used for example in the plastics industry.

Preferred organic boron compounds are boron esters having melting points in the desired range. Typical esters which may be used are mono (2-methyl-2,4-pentanediol)monoborate, triethanediol diborate, tri-(2,3-dimethyl-2,3-butanediol) diborate, tri-(2,5-dimethyl-2,5-hexanediol) diborate, tri-(2,6-dimethyl-4-heptanol)borate, triethanolamine borate and tri-iso-propanolamine borate. These materials are hydrolysed in the presence of the moisture typically found in timber and other structural materials to yield boric acid and the organic component which may be a diol, monohydric alcohol or an alkanolamine. The organic component is miscible with water and penetrates the substrate and acts as a solvent for transporting the boric acid active ingredient and unhydrolysed organic boron compound through the substrate.

It is a particular feature of this invention that the presence of the free organic hydrolysis product facilitates the movement of the boric acid preservative through timber, particularly through the grain, in a manner similar to that described in U.S. Pat. No. 4,610,881 for surface treatment and effectively brings boric acid into all areas susceptible to decay more rapidly than when using shaped products as described in earlier specifications. For example, on hydrolysis a free glycol and solution of boric acid enables diffusion to commence immediately, whereas with an element comprising solid inorganic materials the active ingredient has to dissolve in moisture present in the substrate before diffusion will occur.

Thus in the prior disclosures it is a comparatively slower process for the integrity of the shaped products to disappear. Fast availability of the preservatives is essential to reduce the risk of continued infestations by fungi or insects in remedial treatments and also for protective measures. This early penetration by preservative materials through substrates having moisture contents considered conventional for surface protected timber is valuable in case of early breakdown of surface coating.

In practice, the products of the invention are manufactured preferably in the shape of cylindrical rods or pellets. They are used by establishing a cavity by boring a hole to the desired depth in the substrate to be protected, inserting one or more rods or pellets, and sealing the hole with a cap, plug or conventional filler.

The products of the present invention can be used to advantage in both protective and remedial treatments. In the United Kingdom new joinery typically has an average moisture content of between 12% and 15%. This is maintained under normal circumstances in external conditions where the joinery is protected by an appropriate surface coating. When the joinery is inadequately maintained, the moisture content will rise to about 25-30% and it is only then that conditions are suitable for the germination of fungi such as those causing dry and wet rot which are responsible for most cases of decay.

Within a comparatively short time when brought into contact with the substrate, the products of this invention will commence to disintegrate, initially into a pasty mass which adheres to the walls surrounding the preformed cavity where diffusion occurs through the walls over their whole area into substrate. In time the pasty material diminishes as the boric acid and the organic material diffuses but it can easily be replenished by periodic inspection and insertion of new rods or pellets into the cavity. In practice in timber containing 12-15% moisture, disintegration of the compositions can occur in as little time as a few weeks.

In one aspect of the invention mixtures of organic boron compounds may be used to control the availability of boric acid from the shaped products. Ideally, the protection system should deliver initially a rapid high level amount of preservative to arrest the activity of decay organisms followed by a long term low level release of preservative to maintain protection. Thus a combination of organic boron compounds showing different rates of hydrolysis may be used to vary the rate of diffusion of boric acid through the substrate.

The organic boron compounds used according to this invention typically contain 2.5-7.5% boron which is all available as boric acid as the compounds are totally prone to hydrolysis.

In a second preferred aspect of this invention the available boron can be increased by dispersing water-soluble inorganic borates into the organic boron compounds during manufacture of the shaped elements.

The inorganic borates are preferably selected from alkali metal borates, such as sodium tetraborate or sodium octaborate tetrahydrate, boric acid and boric oxide. In particularly preferred compositions the dispersed inorganic boron compounds are mixtures of discrete particles which have different rates of dissolution in the moisture present in the substrates so as to provide elements giving protection over longer periods. Of these compounds, boric acid is most readily available while boric oxide, being glassy in nature is very slow to dissolve.

An example of a composition of a preferred element in parts by weight comprises:
mono hexylene glycol monborate: 20
boric acid: 20
borax: 30
boric oxide: 30

The ratios between the borate components depends on the rate of dissolution required for a particular application. For example, in damp conditions leaching of water soluble preservatives is more rapid, thus more of a slow dissolving preservative such as boric oxide would be necessary to provide effective protection over long periods.

In general, a ratio of boric oxide to other borates and boric acid of between 10:1 and 1:10 is desirable.

However, this aspect of the invention is not limited to the use of inorganic boron compounds as other water-soluble compounds having fungicidal or insecticidal properties may also be dispersed within the organic boron compound matrix. Examples of suitable compounds are copper, arsenic and chromium salts and fluorides such as sodium fluoride.

It is evident that the more available preservative there is in the shaped elements, the greater the area radiating the element may be protected before decomposition is complete and the preservative leaches from the substrate. Advantageously, we have found that up to five parts by weight of particulate inorganic preservative to one part by weight or organic boron compound can be used without adversely affecting the structure or mechanical stability of the elements during their manufacture or use. Therefore, the organic boron compounds not only provide a more rapid access to boric preservative elements than possible heretofore with solid preservative elements, they are also very effective matrices for dispersing other preservatives to form elements by more economical processes.

The invention will be further illustrated by reference to the following example:

EXAMPLE

Samples of tri-(2,2-dimethyl-1,3-propanediol)diborate and tri-(2,3-dimethyl-2,3-butanediol)diborate were melted and cast into cylindrical rods having a diameter of 13 mm.

Joinery quality pine pieces 450 mm long with dressed dimensions of 44×94 mm were prepared. At the midpoint of each piece a 13 mm hole was drilled through the 94 mm dimension to within 6 mm of the bottom surface. The rods were inserted into the holes with a sufficient upper gap for plugging to enable them to be periodically inspected. Comparative samples were prepared using commercially available rods comprising 67% sodium octaborate tetrahydrate preservative.

Replicate pieces were stacked in layers, with wooden stickers placed between each layer, in thermostatically controlled air circulation cabinets having relative humidities of 65% and 100% respectively. These gave average moisture contents in the timber pieces of approximately 12% and 24% for the duration of the tests.

At monthly intervals over an exposure period of six months, the timber pieces were examined to establish the condition of the rods and diffusion distance of boron using the curcumin test. The results obtained are shown in the following Table 1.

TABLE 1

| Sample | Time Mths | Diffusion distance mm 65% RH | Diffusion distance mm 100% RH | Condition of rod 65% RH | Condition of rod 100% RH |
|---|---|---|---|---|---|
| | 1 | 25 | 50 | disintegrated[c] | disintegrated |
| Tri-(2,2-dimethyl-1,3- | 3 | 75 | 75[a] | small residue[c] | small residue |
| propanediol)diborate | 5 | 75 | 75 | small residue | small residue |
| | 6 | 75 | 75 | small residue | small residue |
| | 1 | 50 | 75 | disintegrated | disintegrated |
| Tri-(2,3-dimethyl-2,3- | 3 | 50 | 75[a] | small residue | small residue |
| butanediol)diborate | 5 | 50 | 75 | small residue | small residue |
| | 6 | 75 | 75 | small residue | small residue |
| Sodium octaborate tetrahydrate | 6 | —[b] | —[b] | largely unchanged | largely unchanged |

[a]Increase in lateral diffusion over cross-section
[b]No indication at 25 mm
[c]disintegrated - reduced volume with crumbly texture small residue - largely dissipated, small quantity of residual material

EXAMPLE II

Samples of mono(2-methyl 2,4-pentanediol) monoborate and tri-(2,3-dimethyl-2,3 butanediol)diborate were melted and cast into cylindrical rods having a diameter of 13 mm. Similar samples were prepared using these compounds, but with the incorporation of finely divided inorganic boron compounds as indicated in Table 2 prior to casting.

These Samples were obtained by melting the organic boron compound and adding the inorganic boron compound to the melt. The pourable mix was then cast into rods as before.

Rods were inserted into pine pieces and placed in thermostatically controlled air circulation cabinets as described in Example I.

The rods were examined bimonthly over an exposure period of six months. The results obtained are shown in Table 2.

TABLE 2

| Sample | Boron Content (wt. %) | Time (Months) | Diffusion Distance mm 65% RH | Diffusion Distance mm 100% RH | Condition of Rod 65% RH | Condition of Rod 100% RH |
|---|---|---|---|---|---|---|
| Mono(2-methyl-2,4-pentanediol) monoborate | 7.24 | 2 | — | 25 | no visable change | some powdering |
| | | 4 | 25 | 50 | powdering exterior | powdery exterior |
| | | 6 | 25 | 50 | powdering exterior | powdery exterior |
| Mono(2-methyl-2,4-pentanediol monoborate) (1 part) and boric acid (2 parts) | 14.00 | 2 | — | 25 | some powdering | some powdering |
| | | 4 | 25 | 50 | powdery exterior | powdery exterior |
| | | 6 | 25 | 50 | powdery exterior | powdery exterior |
| tri-(2,3-dimethyl-2,3-butanediol) diborate | 6.15 | 2 | 75 | 75 | small residue | small residue |
| | | 4 | 100 | 100 | small residue | small residue |
| | | 6 | 100 | 100 | small residue | small residue |
| tri-(2,3-dimethyl-2,3-butanediol) diborate (2 parts) and boric oxide (3 parts) | 21.10 | 2 | — | 25 | some powdering | soft texture |
| | | 4 | 25 | 50 | pasty exterior | pasty throughout |
| | | 6 | 25 | 50 | pasty exterior | pasty throughout |

Various modifications and changes of the invention can be made and, to the extent that such variations incorporate the spirit of this invention, they are intended to be included within the scope of the appended claims.

What is claimed is:

1. A shaped preservative element in the form of a rod or pellet, for timber or masonry, which contains a solid organic boron ester having a melting point of about 50°-200° C., which is hydrolysable in the presence of water.

2. An element as claimed in claim 1 wherein the boron ester is selected from mono(2-methyl-2,4-pentanediol)monoborate, triethanediol diborate, tri-(2,3-dimethyl-2,3-butanediol)diborate, tri-(2,5-dimethyl-2,5-hexanediol)diborate, tri-(2,6-dimethyl-4-heptanol)borate, triethanolamine borate and tri-isopropanolamine borate.

3. An element as claimed in claim 1 wherein a combination of two or more organic boron compounds having different rates of hydrolysis are contained in the element.

4. An element as claimed in claim 1 wherein said organic boron ester contains between 2.5 and 7.5% boron by weight.

5. An element as claimed in claim 1 wherein a water-soluble inorganic boron compound is incorporated into the element with the organic boron ester.

6. An element as claimed in claim 5 wherein the inorganic boron compound is one or more of alkali metal borates, boric oxide and boric acid.

7. An element as claimed in claim 6 wherein boric acid and other borates are present in a weight ratio between 1:10 and 10:1.

8. An element as claimed in claim 1 wherein other water-soluble compounds having fungicidal or insecticidal properties are incorporated into the element.

9. An element as claimed in claim 8 wherein the water-soluble compound is selected from metal salts of copper, arsenic or chromium and inorganic fluorides.

10. A method of preserving masonry or timber against attack by fungus or insects comprising forming a cavity in the relevent masonry or timber member, inserting a shaped element in said cavity, and then covering the element with a cap, plug or filler, wherein said element is in the form of a rod or pellet and comprises a solid organic boron ester having a melting point of about 50°-200° C. which is hydrolysable in the presence of water.

11. A method according to claim 10 wherein said element is a boron ester selected from mono (2-methyl-2,4-pentanediol)monoborate, triethanediol diborate, tri-(2,3-dimethyl-2,3-butanediol) diborate, tri-(2,5-dimethyl-2,5-hexanediol) diborate, tri-(2,6-dimethyl-4-heptanol)borate, triethanolamine borate and tri-isopropanolamine borate.

12. The method according to claim 10 in which a combination of two or more organic boron compounds having different rates of hydrolysis are contained in the element.

13. The method according to claim 10 wherein a water-soluble inorganic boron compound is incorporated into the element with the organic boron compound.

14. An element as claimed in claim 1 in which said solid organic boron ester is mono(2-methyl-2,4-pentanediol)monoborate.

15. An element as claimed in claim 1 in which said solid organic boron ester is tri-(2,3-dimethyl-2,3-butanediol)diborate.

16. An element as claimed in claim 1 in which said solid organic boron ester is tri-(2,2-dimethyl-1,3-propanediol)diborate.

17. The method according to claim 10 in which said solid organic boron ester is mono(2-methyl-2,4-pentanediol)monoborate.

18. The method according to claim 10 in which said solid organic boron ester is tri-(2,3-dimethyl-2,3-butanediol)diborate.

19. The method according to claim 10 in which said solid organinc boron ester is tri-(2,2-dimethyl-1,3-propanediol)diborate.

20. A preservative composition comprising
mono(2-methyl-2,4-pentanediol)monoborate: 20 parts
boric acid: 20 parts
borax: 30 parts
boric oxide: 30 parts
said parts by weight.

* * * * *